United States Patent [19]

Gross et al.

[11] Patent Number: 4,478,944
[45] Date of Patent: Oct. 23, 1984

[54] ANALYTICAL ELEMENT CONTAINING A BARRIER ZONE AND PROCESS EMPLOYING SAME

[75] Inventors: Robert C. Gross; Susan C. Gross, both of Rochester, N.Y.

[73] Assignee: Eastman Kodak Company, Rochester, N.Y.

[21] Appl. No.: 444,112

[22] Filed: Nov. 24, 1982

[51] Int. Cl.³ .................... G01N 21/78; G01N 33/52; G01N 33/66

[52] U.S. Cl. ..........................: ................. 436/95; 422/56; 435/805; 436/170

[58] Field of Search .................. 436/169, 170, 95; 422/56, 57, 58; 435/805

[56] References Cited

U.S. PATENT DOCUMENTS

| | | |
|---|---|---|
| 3,011,874 | 12/1961 | Deutsch . |
| 3,459,790 | 8/1969 | Smith . |
| 3,552,925 | 1/1971 | Fetter . |
| 3,552,928 | 1/1971 | Fetter . |
| 3,663,374 | 5/1972 | Moyer et al. . |
| 3,852,073 | 12/1974 | Fitzgerald . |
| 3,888,669 | 6/1975 | Cardone . |
| 3,992,158 | 11/1976 | Przybylowicz et al. . |
| 4,042,335 | 8/1977 | Clement . |
| 4,066,403 | 1/1978 | Bruschi . |
| 4,110,079 | 8/1978 | Schaeffer et al. . |
| 4,166,093 | 8/1979 | Smith-Lewis et al. . |
| 4,189,304 | 2/1980 | Adams, Jr. et al. . |
| 4,215,195 | 7/1980 | Ponticello et al. . |
| 4,233,029 | 11/1980 | Columbus . |
| 4,247,673 | 1/1981 | Ponticello et al. . |
| 4,250,257 | 2/1981 | Lee et al. . |
| 4,254,083 | 3/1981 | Columbus . |
| 4,255,384 | 3/1981 | Kitajima et al. . |
| 4,256,693 | 3/1981 | Kondo et al. . |
| 4,258,001 | 3/1981 | Pierce et al. . |
| 4,260,393 | 4/1981 | Gibson . |
| 4,271,119 | 6/1981 | Columbus . |
| 4,302,313 | 11/1981 | Columbus . |
| 4,310,399 | 1/1982 | Columbus . |
| 4,317,892 | 3/1982 | Abel . |
| 4,323,536 | 4/1982 | Columbus . |
| 4,363,874 | 12/1982 | Greenquist ........................ 422/57 X |
| 4,390,343 | 6/1983 | Walter ............................. 422/57 X |

FOREIGN PATENT DOCUMENTS

| | | |
|---|---|---|
| 10425 | 4/1980 | European Pat. Off. . |
| 28123 | 5/1981 | European Pat. Off. . |
| 54-129790 | 10/1979 | Japan . |
| 911181 | 11/1962 | United Kingdom . |
| 922665 | 4/1963 | United Kingdom . |
| 1037155 | 7/1966 | United Kingdom . |
| 1316541 | 5/1973 | United Kingdom . |
| 2069131 | 8/1981 | United Kingdom . |
| 2069132 | 8/1981 | United Kingdom . |

Primary Examiner—Arnold Turk
Attorney, Agent, or Firm—J. Lanny Tucker

[57] ABSTRACT

A multizone element, for quantitative analyte determination in whole blood, containing a porous spreading zone separated from a reagent zone by a barrier zone, said barrier zone comprising a non-porous film comprising a polymer of: from 30 to 95 percent by weight of polymerized monomer having the structure

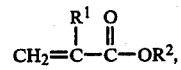

from 0.25 to 30 percent by weight of polymerized monomer having the structure

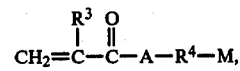

from 0.1 to 50 percent by weight of polymerized monomer having the structure

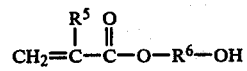

wherein:
$R^1$, $R^3$, and $R^5$ are independently selected from the group consisting of hydrogen and methyl,
$R^2$ is alkyl of from 1 to 16 carbon atoms,
$R^4$ and $R^6$ are independently selected from the group consisting of alkylene groups having from 1 to 6 carbon atoms,

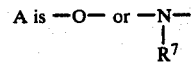

wherein $R^7$ is hydrogen, alkyl of 1 to 10 carbon atoms, or cycloalkyl of 5 to 10 carbon atoms, and
M is $NR^8R^9H^+X$ or $SO_3^-X$ wherein $R^8$ and $R^9$ are independently selected from the group consisting of hydrogen and alkyl of 1 to 4 carbon atoms and X is a counterion.

A process for employing the element in analyses for analytes in whole blood is also disclosed.

14 Claims, No Drawings

ANALYTICAL ELEMENT CONTAINING A BARRIER ZONE AND PROCESS EMPLOYING SAME

BACKGROUND OF THE INVENTION

1. Field of the Invention

The present invention relates to non-porous films. More particularly, the present invention relates to the use of non-porous films in analytical elements whereby analytes in samples of whole blood are separated from substances that can interfere with the desired analysis.

2. Description of Related Art

Various analytical elements for clinical analysis have been proposed using "dry chemistry", i.e., analytical clinical techniques wherein chemical reagents are incorporated in various substantially "dry-to-the-touch" elements, such as test strips and multizone analytical test elements.

U.S. Pat. No. 3,992,158 issued Nov. 16, 1976 discloses improved multizone analytical elements for the analysis of liquids via "dry chemistry". In the element disclosed, there is present a reagent zone and a spreading zone. When the spreading zone of the element was spotted with a sample of aqueous liquid to be tested for a particular analyte, this zone was found to be especially effective in receiving the liquid test sample and distributing such liquid within itself in a manner to provide a substantially uniform concentration of analyte for interaction with the reagent components of the element. The reagent zone contains any of a variety of compositions interactive with the desired analyte to provide, for example, a radiometrically detectable species indicative of the presence and/or concentration of the analyte. These analytical elements are used in the analysis of a variety of blood components including glucose, uric acid, and protein, e.g. albumin.

In these elements, the spreading zone pore size is generally chosen so that the zone filters out undesirable sample components that interfere with an analytical reaction or with detection of any test result produced within the element. It is taught that for analysis of whole blood, porous zones having a pore size of from 1 to about 5 microns are particularly useful in screening out blood cells. Also, a filter or dialysis zone can be included at an appropriate location in the element. It is stated that in analyzing for blood glucose, a dialysis zone, such as a semi-permeable cellulose membrane, can prevent passage of proteins and other potentially interfering substances to the reagent zone.

U.S. Pat. No. 4,258,001 issued Mar. 24, 1981, describes elements that have, as a spreading layer, a particulate structure comprising (1) a plurality of heat-stable, organopolymeric particles non-swellable in, and impermeable to, the liquid under analysis and (2) an adhesive for these particles. These layers can be used along with one or more separate functional zones permeable to the liquid under analysis, such as reagent zones, registration zones, radiation-blocking zones, and selectively permeable barrier zones. These optional zones can include, among others, filtering zones to filter out or remove particular components of applied liquid samples, as described in U.S. Pat. No. 3,992,158, and barrier compositions having a predetermined selective permeability permitting only selected species to come into fluid contact with particular zones of the multizoned element, such barrier compositions being described in U.S. Pat. No. 4,066,403 issued Jan. 3, 1978. These elements can be used to analyze either serum, plasma, or whole blood. The barrier compositions described in U.S. Pat. No. 4,066,403 that are specifically mentioned therein are cellulose acetate butyrate, cellulose propionate valerate, poly(methylmethacrylate), and cellulose acetate.

Published European Patent Applicaton No. 10425 is directed to a semi-permeable composite membrane comprising a thin semi-permeable film of a polymeric material deposited on one side of a microporous substrate. The polymeric material is prepared by cross-linking a soluble polymer containing at least 30 mole% of a recurring unit of the formula

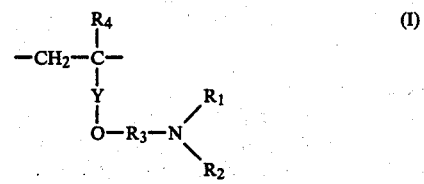

wherein, for example, among a number of possibilities, Y can be a carbonyl group

$R_1$ can be a hydrogen atom or a monovalent organic radical containing 1 to 20 carbon atoms;

$R_2$ can be a hydrogen atom;

$R_3$ can be an alkylene group containing 2 to 5 carbon atoms; and $R_4$ can be a hydrogen atom or a methyl group. Cross-linking is carried out through the amino group by means of a polyfunctional compound.

These membranes can be used for reverse osmosis. It is said that reverse osmosis can be used for removing impurities from liquids such as water or blood. The polymer used in preparing the semi-permeable membranes can be a copolymer containing up to 70 mole% of one or more comonomers. These polymers can be blended with up to 50 mole % of another polymer having the ability to form a water-soluble or aqueous emulsion. The polymer is deposited on a microporous substrate by applying a solution of the base polymer to the substrate. After such deposition, the polymer is cross-linked.

Recently, the Fuji Photo Film, Co., Ltd., has described multizone elements for blood analysis in the patent and technical literature, e.g., Clinical Chemistry, Vol. 27, No. 7, 1981, 1287-1290; U.S. Pat. No. 4,256,693; U.S. Pat. No. 4,255,384; and U.K. patent application Nos. 2,069,131 A and 2,069,132 A, both published Aug. 19, 1981.

The Clinical Chemistry article describes an element for determining glucose in whole blood. The element consists of a spreading zone, a blocking zone, an enzymic reagent zone, and a transparent support zone. It is said that blood cells and platelets are filtered off through the fibrous structure of the spreading zone, but that blood plasma diffuses through to the blocking zone. Diffusion of macromolecules and hydrophobic substances bound to proteins in a plasma are reported to be blocked at the blocking zone, thereby not reaching the reagent zone. It is also said that the blocking zone further serves as a reflector for reflection densitometry and a shield from interference by colored materials in blood such as hemoglobin and bilirubin on the spreading zone.

Japanese Kokai 129790/79 relates to a filter for separating leucocytes that comprises a polymer containing at least 1.0% by weight of (A) and/or (B) below.

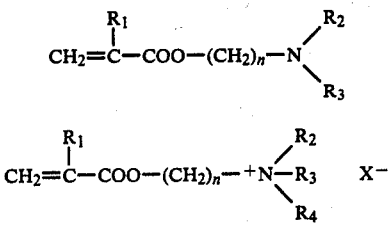

wherein
$R_1$ represents H or $CH_3$; $R_2$, $R_3$, and $R_4$ each represents H, $CH_3$, $C_2H_5$ or $C_3H_7$; X represents Cl, OH, Br, I or $NO_3$; and n is an integer of 1 to 30, the filter being packed with the polymer.

As a comonomer there can be used any monomer than can be copolymerized with at least 1% by weight of (A) or (B). In use, the polymer is fashioned into a thread-like or granular form and placed in a column. The leucocytes remain in the filter and the erythrocytes are hemolyzed and pass through the filter along with the plasma.

Other semi-permeable membranes capable of separating desired substances from the many components of whole blood have also been described, including gelatin (U.K. Published Application No. 2,069,131 A), cellulose or cellulose derivatives (U.K. Pat. No. 911,181), and ethyl cellulose (U.K. Pat. No. 922,665).

Many of these materials, as well as others (see Examples 5–8, infra), were tested by us in an effort to provide an improved element of the "dry assay" type for the determination of analytes, particularly glucose, in whole blood. None, however, were satisfactory. In some instances, the membranes were too permeable; in others, they were not permeable enough. In either case, the result was an inability to differentiate meaningfully among various analyte concentration levels. Thus, a need remains for analytical elements of the type used in so-called "dry assays", that are improved by the inclusion therein of barrier zones particularly suited for separating analytes from the several interferents present in whole blood.

SUMMARY OF THE INVENTION

The present invention relates to improved elements and processes for the quantitative determination of one or more analytes in whole blood. By virtue of the present invention, the problem referred to in the previous paragraph has been solved and "dry assay" type elements and processes are now provided from which a meaningful determination of analyte concentration in whole blood samples can be obtained. The problem has been solved by use of a non-porous film of a particular chemical composition as a barrier zone in the analytical element.

More particularly, the present invention relates to a multizone element, for quantitative analyte determination in whole blood, containing a porous spreading zone separated from a reagent zone by a barrier zone, the barrier zone comprising a non-porous film comprising a polymer of: from 30 to 95% by weight of polymerized monomer having the structure

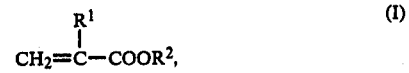

from 0.25 to 30% by weight of polymerized monomer having the structure

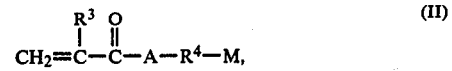

from 0.1 to 50% by weight of polymerized monomer having the structure

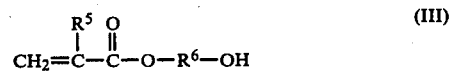

where
$R^1$, $R^3$, and $R^5$ are independently selected from the group consisting of hydrogen and methyl;
$R^2$ is alkyl of from 1 to 16 carbon atoms;
$R^4$ and $R^6$ are independently selected from the group consisting of alkylene groups having from 1 to 6 carbon atoms;

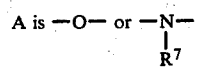

where
$R^7$ is hydrogen, alkyl of 1 to 10 carbon atoms, or cycloalkyl of 5 to 10 carbon atoms, and
M is $NR^8R^9H^+X$ or $SO_3^-X$, where $R^8$ and $R^9$ are independently selected from the group consisting of hydrogen and alkyl of 1 to 4 carbon atoms and X is a counterion.

In another aspect, the present invention relates to a process for quantitative analyte determination in whole blood comprising bringing a sample of the blood into contact with a multizone element containing a porous spreading zone separated from a reagent zone by a barrier zone comprising a non-porous film of a polymer as described above.

Description of the Preferred Embodiments

The analytical elements of the present invention comprise at least three zones: a spreading zone, a barrier zone, and a reagent zone, i.e., a zone in which an analyte or reaction product thereof is acted upon in some way to bring about, either directly or indirectly, a detectable change.

A sample applied to the element is first distributed uniformly by the spreading zone so as to present a uniform concentration of material to the adjacent zones, as disclosed, for example, in U.S. Pat. No. 3,992,158. The spreading zone is generally the zone upon which the liquid sample to be analyzed, i.e. whole blood, is deposited.

The particular morphology of the spreading zone is not critical to the practice of the present invention. Any configuration that will provide a means by which the sample or a portion thereof is distributed and presented uniformly to the adjacent zones can be employed. For example, for some applications, the spreading zone is a fibrous porous membrane, such as of the type described in U.K. patent application Nos. 2,069,131 A or 2,069,132 A, which comprises a fibrous porous material, such as a fabric. Such fabrics can be rendered hydrophilic as described in U.K. Pat. No. 2,013,338, may be knitted or woven, and can be composed of natural or synthetic fibers or mixed yarns.

Alternatively, the spreading zone can be an enclosed capillary chamber between two spaced-apart surfaces wherein the sample is spread by capillary flow. Such devices are known in the art and have been described, for example, in U.S. Pat. No. 4,233,029; U.S. Pat. No. 4,254,083; U.S. Pat. No. 4,271,119; U.S. Pat. No. 4,302,313; U.S. Pat. No. 4,310,399; and U.S. Pat. No. 4,323,536.

As another alternative, the spreading zone can be in the form of a porous layer, preferably an isotropically porous layer of the type described, for example, in U.S. Pat. No. 3,992,158 or U.S. Pat. No. 4,258,001, wherein "isotropically porous" refers to substantial porosity in all directions within the zone.

Furthermore, the elements of the present invention can contain more than one spreading zone and, where this is the case, the several zones can be of the same or different configuratons and compositions.

A convenient method of determining whether a particular zonal configuration is suitable for spreading purposes includes densitometric or other analytical techniques, as by scanning the appropriate surface or reagent zone or other associated zone to determine the concentration of spread substance or of any reaction product based on the concentration of spread substance. One such method is described in detail in U.S. Pat. No. 3,992,158.

Where the spreading zone is in the form of an isotropically porous layer, particulate material can be used to form the layer, the isotropic porosity being created by interconnected spaces among the particles. If a particulate material of choice is not adherent, it can be treated to form particles that adhere to each other at points of contact.

As an alternative or in addition to such particulate materials, the spreading zone can be prepared using isotropically porous polymers. It is possible to prepare such polymers using techniques useful in forming "blush" polymers as described in U.S. Pat. No. 3,992,158.

It is also desirable to include within an element one or more reflective zones, optionally absorptive to detecting radiation, to facilitate result detection by reflection radiometry, e.g., reflection photometry or a similar technique. Pigments, such as titanium dioxide and barium sulfate, are reflective and can be used to advantage in a reflecting zone.

As mentioned above, the spreading zone can also be one of the type described in U.S. Pat. No. 4,258,001. Such spreading zones have a particulate structure comprising a plurality of heat-stable, organopolymeric particles, non-swellable in, and impermeable to, the liquid under analysis and an adhesive for these particles comprising an organic polymer different from that of the particles. The adhesive is concentrated on the surface of the heat stable particles in areas contiguous to adjacent particles and bonds the particles into a coherent three-dimensional lattice that is non-swellable in the liquid under analysis. This lattice contains interconnected voids among the particles to provide transport of the aqueous liquid and to render the lattice isotropically porous.

The reagent zone of the improved elements of the present invention is of the type described in a number of patents assigned to the Eastman Kodak Company. See, for example, U.S. Pat. No. 3,992,158 and U.S. Pat. No. 4,042,335. This reagent zone is permeable at least to the analyte being determined and contains a composition comprising a material that is interactive in the presence of the analyte or a reaction product of the analyte to provide, either directly or indirectly, a detectable species, such as a dye.

The reagent zone can employ a fibrous reagent matrix, such as filter paper, woven fabric, fibrous fleece, or matting. Non-fibrous reagent zones are, however, considered optimal for quantitative measurements. Such zones generally have a hydrophilic colloid reagent matrix.

The reagent zones are desirably uniformly permeable to the analyte or reaction product thereof and, optionally, porous. As used herein, the term "permeability" includes permeability arising from porosity, ability to swell, or similar characteristics.

Reagent zones can include a matrix in which the interactive material is distributed, i.e., dissolved or dispersed. The choice of the matrix material is, of course, variable and dependent on the intended use of the element. Desirable matrix materials for reagent zones can include hydrophilic materials including both naturally occurring substances such as gelatin, gelatin derivatives, hydrophilic cellulose derivatives, polysaccharides such as dextran, gum arabic, and agarose, and synthetic substances, such as water-soluble polyvinyl compounds such as polyvinyl alcohol and polyvinyl pyrrolidone, and acrylamide polymers. Organophilic materials, such as cellulose esters, are also useful and the choice of materials, in any instance, reflects the use for which a particular element is intended. To enhance permeability of the reagent zone, it is often useful to employ a matrix material that is swellable in the solvent or dispersion medium of the liquid under analysis. Also, it may be desirable to select a material that is compatible with the application of an adjacent zone, such as by coating means, during manufacture of the element.

Within the reagent zone is distributed a composition, including one or more active materials, that is interactive in the presence of the analyte. Optionally, the interactive composition also interacts with a reaction product of such an analyte, if appropriate in view of the analysis of choice. The term "interactive" refers to chemical reactivity, catalytic reactivity, as in the formation of an enzyme-substrate complex, or any other form of chemical or physical interaction capable of producing or promoting within the element the formation of a species that is detectable.

Reagents or other interactive materials soluble in the liquid under analysis may advantageously be immobilized in the reagent zone, particularly when the reagent zone is porous.

Particular interactive materials that may be distributed within a reagent zone depend upon the analysis of choice. In the case of many analyses, enzymes, such as oxidase materials like glucose oxidase or cholesterol oxidase, may desirably be included as interactive materials within a reagent zone of an element intended for the analysis of analyte that is a substrate for such enzyme. As an example, an oxidative enzyme, e.g. glucose oxidase, can be incorporated into a reagent zone together with peroxidase or a peroxidative material and a material or composition that, upon oxidation in the presence of oxidase (or another substance having peroxidative activity) and the hydrogen peroxide formed upon interaction of the oxidase and its substrate, provides a dye or other detectable species.

The detectable species may be diffusible so that it can move into a permeable registration zone, if such zone is present. Such diffusivity can be imparted to detectable species not inherently diffusible by means known to those skilled in chemical synthesis, generally by the addition of chemical groups that impart solubility.

Materials or compositions that contain an oxidizable material and can provide a detectable species include certain dye providing compositions. In one aspect, dye providing compositions include a compound that, when oxidized, can couple with itself or with its reduced form to provide a dye. Such auto coupling compounds include a variety of hydroxylated compounds, such as o-aminophenols, 4-alkoxynaphthols, 4-amino-5-pyrazolones, cresols, pyrogallol, guaiacol, orcinol, catechol, phloroglucinol, p-dihydroxydiphenylgallic acid, pyrocatechoic acid, and salicyclic acid. Compounds of this type are well known and described in the literature, such as in *The Theory of the Photographic Process*, Mees and James, 3rd Edition, 1966, especially in Chapter 17.

Particularly preferred dye-providing materials are the triarylimidazoles described in U.S. Pat. No. 4,089,747.

In another aspect, the detectable species can be provided by oxidation of a leuco dye to provide the corresponding dyestuff form. Representative leuco dyes include such substances as leucomalachite green and leucophenolphthalein. Other leuco dyes, termed oxichromic compounds, are described in U.S. Pat. No. 3,880,658.

In yet another aspect, the detectable species is formed by dye-providing compositions that include the condensation products of oxidizable compounds with couplers. Representative oxidizable compounds include benzidine and its homologs, p-phenyldiamines, p-aminophenols, 4-amino-antipyrine, and the like. A wide range of such couplers including a number of auto coupling compounds, is described in the literature, such as in Mees and James, supra, and in Kosar, *Light Sensitive Systems*, 1965, pages 215-249.

The spreading zone and the reagent zone of the improved elements of the present invention are separated by a barrier zone. They may be separated by additional zones as well. As noted above, the barrier zone is in the form of a non-porous synthetic polymer film.

By "non-porous" is meant that the films employed as barriers in the present invention are not of the type described as "microporous membranes" in the Encyclopedia of Polymer Science and Technology, Vol. 8, 1968, page 620. Such microporous membranes are described as having a structure that enables liquids to flow through them according to the normal equations of hydrodynamics and an effective pore size at least several times the mean free path of the molecules, i.e. from several micrometers down to about 100 A (10 nm). Of course, films are considered porous, as used herein, if they also have pores larger than this. Although the mechanism of transport through the barrier zone of the elements of the present invention is not known, it is believed that the non-porous films used are of the type described on pp. 620 and 621 of the above reference as being "molecular diffusion membranes" or "ultrafilter type membranes". The effective pore size of ultrafilter type membranes is from about 7 to 50 A (0.7 to 5 nm). The "molecular diffusion membranes" have no pores at all in the strict sense of the word.

The barrier zones are at least partially permeable to the analyte being determined and are impermeable to interferents for such determination, e.g. hemoglobin. It is understood that the terms "permeable" and "impermeable" as used herein are employed in the practical sense of permeability or impermeability during the time period over which the analyte determination takes place.

The polymer that the barrier zone comprises can be prepared by the polymerization of a mixture of monomers comprising from 30 to 95% by weight

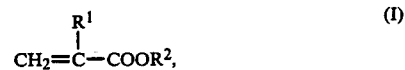

from 0.25 to 30% by weight

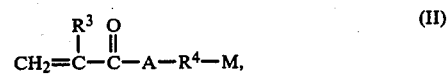

from 0.1 to 50% by weight

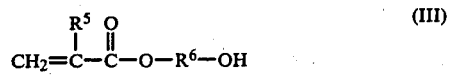

where
$R^1$, $R^3$, and $R^5$ are independently selected from the group consisting of hydrogen and methyl;
$R^2$ is alkyl of from 1 to 16 carbon atoms;
$R^4$ and $R^6$ are independently selected from the group consisting of alkylene groups having from 1 to 6 carbon atoms;

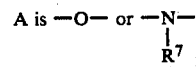

where
$R^7$ is hydrogen, alkyl of 1 to 10 carbon atoms, or cycloalkyl of 5 to 10 carbon atoms, and
M is $NR^8R^9H^+X$ or $SO_3^-X$,
where $R^8$ and $R^9$ are independently selected from the group consisting of hydrogen and alkyl of 1 to 4 carbon atoms and X is a counterion.

The composition of these polymers has here been described with reference to the percentage by weight of the monomers that enter the polymerization reaction. It will be understood by those skilled in the art that, in general, the weight percentage of the individual polymerized monomers in the resulting polymer will not be exactly the same as the percentages given above. These differences are generally fairly small, however, i.e. on the order of 1 or 2 percentage points.

In addition to the above, other units derived from additional monomers can also be present if desired, in order to modify the properties of the polymer for special requirements.

Polymers containing units polymerized from monomer (II) are known in the art. See, for example, U.S. Pat. No. 2,923,734; U.S. Pat. No. 3,024,221; U.S. Pat. No. 3,411,911; Japanese Kokai No. 51-130217; U.S. Pat.

No. 3,679,425; Japanese Kokai No. 54-129790; U.S. Pat. No. 4,130,524; Russian Pat. No. 530887; Japanese Kokai No. 54-101791; Japanese Kokai No. 53-16042; Japanese Kokai No. 52-146443; European Published Application No. 10425; Japanese Kokai No. 52-22088; U.S. Pat. No. 3,706,564; U.S. Pat. No. 3,749,577; U.S. Pat. No. 3,813,251; and U.S. Pat. No. 4,055,469. Methods for polymerization are also disclosed.

In the formula

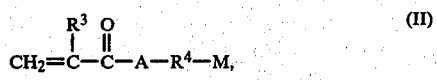

$R^3$ is either hydrogen or methyl and A is either

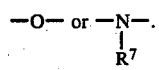

That is to say, the monomer can be considered to be either an ester or an amide of acrylic or methacrylic acid. Where the monomer is an amide, $R^7$ is hydrogen, alkyl of 1 to 10 carbon atoms, i.e. methyl, ethyl, propyl, butyl, pentyl, hexyl, heptyl, octyl, nonyl, decyl, or an isomer of the foregoing, e.g. isobutyl, neopentyl, or ethylhexyl; or cycloalkyl of 5 to 10 carbon atoms, e.g. cyclopentyl, cyclohexyl, cycloheptyl, cyclooctyl, cyclononyl, cyclodecyl, methylcyclopentyl, diethylcyclohexyl, or propylcycloheptyl.

M designates $NR^8R^9H^+X$ or $SO_3^-X$. Thus, these polymerized monomers are in the form of an amine salt or a sulfonate salt. In the case of the amine salt, it is preferred that the salt be the hydrohalide, especially the hydrochloride. Where the polymerized monomer contains a sulfonate group, it will generally be convenient for it to be in the form of an alkali metal salt, such as $Na^+$ or $K^+$, although other salts can be used as long as the monomer retains water solubility. Thus, X can be a positively charged ion such as $Na^+$, $K^+$, or $H^+$ or a negatively charged ion such as chloride, sulfonate, or the like.

As stated above, $R^8$ and $R^9$ are independently selected from the group consisting of hydrogen and alkyl of 1 to 4 carbon atoms, i.e. methyl, ethyl, propyl, butyl, or isomers of the foregoing. It is preferred that at least one of $R^8$ and $R^9$ be hydrogen and most preferred that they both be hydrogen.

Finally, $R^4$ in the above formula represents an alkylene group having from 1 to 6 carbon atoms, i.e., methylene, ethylene, propylene, butylene, pentylene, hexylene, or isomers of the foregoing. $R^4$ can, of course, be substituted, if desired, with any non-interfering substituent. In the above formula, it is preferred that A be oxygen; it is more preferred that A be oxygen and $R^4$ be ethylene; it is most preferred that A be oxygen, $R^4$ be ethylene and $R^3$ be methyl.

As noted above, polymerized monomer (II) constitutes from about 0.25 to 30 percent by weight of the polymer. When the monomer is derived from sulfonic acid or sulfonate salt group containing acrylic monomers (such as 2-methacryloyloxyethyl-1-sulfonic acid, sodium salt), it is preferred that this monomer be employed in a range from 1 to 25 percent by weight and most preferred that it be employed in the range of from 2 to 5 percent by weight. When the monomer is derived from an amine salt of an acrylic or methacrylic amide or ester (such as 2-aminoethyl methacrylate hydrochloride), the preferred range is from 2 to 30 percent by weight and most preferably from 5 to 20 percent.

Where monomer (II) is a sulfoester, it can be prepared using any method known to be suitable. For example, in U.S. Pat. No. 2,923,734, it is disclosed that an α-methylene carboxylic acid and an aliphatic hydroxy sulfonic acid in the free form are interacted by heating, optionally while dispersed in an inert liquid medium capable of forming an azeotrope with water and while azeotropically distilling water out of the reaction mixture to form the corresponding carboxylate ester. The reaction is generally carried out at a temperature between 50° and 200° C. In U.S. Pat. No. 3,024,221, there is disclosed a method for preparing the sulfoesters by reacting the appropriate acyl halide with the salt of a hydroxy sulfonic acid, generally at a temperature in the range of 0° to 200° C., although the particular temperature employed depends upon the nature of the specific reactants. Examples of hydroxy sulfonic acids (and their salts) that can be employed to form the sulfoesters include 2-hydroxyethane sulfonic acid, 2-hydroxy-1-propane sulfonic acid, and 1-hydroxy-2-butane sulfonic acid. α-Methylenecarboxylic acids or acyl halides include, for example, acrylic acid, methacrylic acid, acryloyl chloride, and methacryloyl bromide.

Where monomer (II) is a sulfonate or sulfoamide, it is preferred that it be selected from the group consisting of 2-methacryloyloxyethyl-1-sulfonic acid, sodium salt; sodium 3-acryloyloxypropane-sulfonate; and sodium 2-acrylamido-2-methylpropane sulfonate.

Where monomer (II) is an amine salt of an acrylic or methacrylic amide or ester, it is prepared by the neutralization of the appropriate primary, secondary, or tertiary amine. It is preferred that a primary amine be used. Such amines, as pointed out above, are known in the art and include, for example, aminoethyl acrylate, aminoethyl methacrylate, aminomethyl acrylate, aminomethyl methacrylate, aminobutyl acrylate, N-methylamino ethyl methacrylate, N-ethylaminomethyl acrylate, and N,N-diethylaminoethyl methacrylate. Where monomer (II) is an amine salt, it is preferred that it be 2-aminoethyl methacrylate hydrochloride.

In the formula

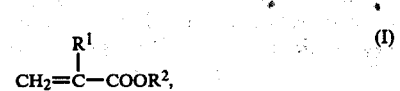

$R^1$ is hydrogen or methyl and $R^2$ is an alkyl group of from 1 to 16 carbon atoms, i.e. methyl, ethyl, propyl, butyl, pentyl, hexyl, heptyl, octyl, nonyl, decyl, undecyl, dodecyl, tridecyl, tetradecyl, pentadecyl, hexadecyl, or isomers of the foregoing. It is preferred that $R^2$ be butyl, more preferably n-butyl and, most preferably, that $R^2$ be n-butyl and $R^1$ be methyl.

Polymerized monomer (I) constitutes from about 30 to 95 percent by weight of the polymer. Preferably, it is present in the polymer in a range of from about 40 to 75 by weight, more preferably, from about 50 to 70 percent by weight.

In the formula

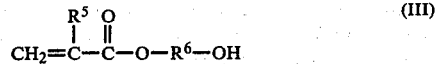

$R^5$ is either hydrogen or methyl and $R^6$ is an alkylene group of from 1 to 6 carbon atoms, i.e. methylene, ethylene, propylene, butylene, pentylene, hexylene, or an isomer of the foregoing. It is preferred that $R^6$ be ethylene and more preferred that $R^6$ be ethylene and $R^5$ methyl.

Polymerized monomer (III) constitutes from about 0.1 to 50 percent by weight of the polymer. Preferably, it is present in an amount of from about 10 to 30 percent by weight, more preferably from about 15 to 25 percent by weight.

As mentioned above, additional polymerized monomers can be included in the polymers of the barrier zones. For example, it has been found useful, although not always necessary, to cross-link the films of these polymers to a small extent in order to control their structural stability in the presence of water. To accomplish this, units can be included in the polymer having moieties, such as hydroxyl groups, carboxyl groups, and active methylene groups, capable of reacting with cross-linking agents. The amine groups of the amine salts described above inherently have such capability. Thus, where the polymers contain one of these amine salts, cross-linking can be carried out by treating the polymer with a cross-linking agent.

In addition to using these amine groups as cross-linking sites, or as an alternative to them where they are not present, as in the above-described polymers containing sulfoester units, additional units in the polymer derived from, for example, monomers containing active methylene groups in their side chains can be included. Such monomers have been described, for example, in U.S. Pat. No. 3,459,790 and U.S. Pat. No. 4,215,195. The polymer can contain up to 20 percent by weight of such polymerized monomers. Preferably, the polymer contains from about 0.1 to 15 percent by weight of these polymerized monomers, more preferably, from about 5 to 10 percent by weight.

Active methylene groups are methylene groups between activating groups, for example, electro-negative groups such as carbonyl. Malonic esters, acetoacetic esters, cyanoacetic esters, and 1,3-diketones are examples of compounds containing such groups. Such monomers include, for example, 2-acetoacetoxyethyl methacrylate or 2-acetoacetoxyethyl acrylate, N-(2-cyanoacetoxyethyl)acrylamide, 4-cyanoacetyl-1-methacryloylpiperazine, N-(2-propionylacetoxybutyl)acrylamide, N-(2-valerylacetoxyphenyl)acrylamide, N-4-(acetoacetoxymethyl)-benzylacrylamide, N-4-(acetoacetoxybenzyl)-phenylmethacrylamide, N-(2-acetoacetoxyethyl)-acrylamide, N-(3-acetoacetamidopropyl)methacrylamide, N-(2-acetoacetamidoethyl)methacrylamide, 4-acetoacetyl-1-methacryloylpiperazine, acetoacetamidoethyl methacrylate, 4-acetoacetyl-1-acryloylpiperazine, N-(2-propionylacetoxyethyl)acrylamide, and N-(2-valerylacetoxypropyl)methacrylamide. The preferred active methylene group-containing monomer used in the polymers employed in this invention is 2-acetoacetoxyethyl methacrylate.

Conventional photographic hardeners can be used as the cross-linking agents to cross-link these polymers. These compounds are well known in the art and an extensive listing of them appears in British Pat. No. 1,478,811 in the paragraph bridging pages 7 and 8 of that patent. Typical hardeners include formaldehyde and free dialdehydes, such as succinaldehyde and glutaraldehyde, blocked dialdehydes, α-diketones, active esters, sulfonate esters, active halogen compounds, s-triazines and diazines, epoxides, aziridines, active olefins having 2 or more active bonds, blocked active olefins, carbodiimides, isoxazolium salts unsubstituted in the 3-position, esters of 2-alkoxy-N-carboxydihydroquinoline, N-carbamoyl and N-carbamoyloxypyridinium salts, halogen-substituted aldehyde acids, 'onium substituted acroleins, and the like (see Research Disclosure; Item 17643; December 1978, page 26). A preferred cross-linking agent for use in the present invention is bis(vinylsulfonylmethyl)ether.

The preferred polymers of the barrier zone of the improved elements of the present invention are synthesized from the following monomers: n-butyl methacrylate, 2-methacryloyloxyethyl-1-sulfonic acid, sodium salt, 2-acetoacetoxyethyl methacrylate, 2-hydroxyethyl methacrylate, 2-aminoethyl methacrylate hydrochloride, and 2-ethylhexyl methacrylate. The preferred polymers include: poly(n-butyl methacrylate-co-2-methacryloyloxyethyl-1-sulfonic acid-co-2-acetoacetoxyethyl methacrylate-co-2-hydroxyethyl methacrylate) (60/5/10/25; 70/2.5/10/17.5; or 60/10/10/20); poly(2-ethylhexyl methacrylate-co-methacryloyloxyethyl-1-sulfonic acid-co-2-acetoacetoxyethyl methacrylate-co-2-hydroxyethyl methacrylate) (50/2.5/10/37.5); and poly(n-butyl methacrylate-co-2-aminoethyl methacrylate hydrochloride-co-2-hydroxyethyl methacrylate) (50/15/35); where the numbers in parentheses are weight percentages of the monomers in the polymerization mixture.

The polymers employed in the practice of the present invention can be prepared at a wide variety of temperatures, since the temperature will depend upon such variable features as the specific monomers used, the duration of heating, pressure employed, and the like. However, the polymerization temperature generally does not exceed about 100° C. and, most often, is in the range of about 50° to about 90° C.

The polymerization is generally carried out in solution in organic solvents, e.g. the lower alcohols, dimethyl sulfoxide, dimethylformamide, and the like, and then, if desired, the polymeric product is dispersed in water. Latex polymerization can also be employed although the barrier properties of the polymers prepared in this way have been inferior to those obtained using solution polymerization.

The pressure employed in the polymerization, if any, is usually only sufficient to maintain the reaction mixture in liquid form, although either superatmospheric or subatmospheric pressures can be used.

The concentration of total polymerizable monomer in the polymerization mixture can be varied widely with concentrations up to about 60 percent by weight and, preferably about 20 to about 40 percent by weight, based on the weight of the monomers plus solvent, being satisfactory.

Suitable catalysts for the polymerization reaction include, for example, the free radical catalysts, such as hydrogen peroxide, cumene hydroperoxide, azo type initiators, and the like. In redox polymerization systems, the usual ingredients can be employed.

If desired, the polymer can be isolated from the reaction solvent by coagulation, or other separation procedures suitable for this purpose, e.g. diafiltration.

Optionally, in forming the barrier zones, these synthetic polymers are blended with various amounts of a hydrophilic colloid, preferably gelatin. The gelatin can constitute up to 70% of the total weight of the polymer and the gelatin. In particular, the inclusion of gelatin in the barrier zones has been found to be especially useful where the synthetic polymer employed is one of the butyl methacrylate/aminoethyl methacrylate hydrochloride/hydroxyethyl methacrylate copolymers referred to above. These polymers have a low permeability, even to the analytes being determined, and it has been found that the presence of gelatin enhances the diffusion of the analyte.

Many advantages are provided by the use of the above-described barrier zones, which can be summarized as follows: (1) Whole blood samples, both hemolyzed and non-hemolyzed, can be analyzed. (2) The barrier zone, which is impermeable to large molecular components for the duration of the test, is only partially permeable to the soluble analytes. This partial permeability offers several advantages, i.e, (a) it provides improved kinetics, i.e. greater linearity, and simplifies calibration of the assay, (b) it permits the assay to be insensitive to metered volume, and (c) it permits the use of a variety of detection systems for chosen analytes not useful prior to the present invention. For instance, dyes having very high extinction coefficients can now be used advantageously. The use of dyes having high extinction coefficients helps to eliminate spectral interferences by enabling the manipulation of the wavelength at which the assay is made.

The semi-permeable barrier zone physically impedes the passage of large molecular components that cause chemical interference for the duration of the test. The zone also has only limited permeability to the analyte. Owing to the minimal quantity of analyte actually passing through the barrier zone and being subsequently detected, the assay is less sensitive to the volume of the sample applied, making it possible to use random quantities of blood samples, such as might be obtained from ear and finger pricks. Also, the small quantity of analyte present permits the use of dyes that have very high extinction coefficients. These high-extinction dyes, heretofore not useful in some assays, permit a greater selection of wavelengths at which the assay can be monitored—ideally, away from the wavelength region of spectral interference. Additionally, the relatively high dye density generated can allow the assay to be spectrally monitored off peak. These options are instrumental in avoiding spectral interferences.

It is necessary that the analytical elements of the present invention contain the above-described spreading, barrier, and reagent zones. Of course, for some applications, it may be desirable to have more than one of these zones, i.e. two or more spreading zones and/or two or more barrier zones and/or two or more reagent zones. This is the case, for example, where a given analyte has to react sequentially with two or more reagents that could, if coated together in one zone, react with each other.

Further, the elements optionally include additional zones having specialized functions required for a given analysis or, perhaps, necessary for the convenient manufacture of the element. For example, it is a common practice to use additional zones where needed in order to promote or control adhesion between other zones. Such zones are commonly referred to as "binder" zones or "subbing" zones and are well known in the art.

Another type of zone that can be employed in these elements, and that is referred to in the examples below, is known as a "gel pad" zone. Such zones comprise gelatin, a surfactant to improve the coatability of the gelatin as a zone, and a conventional hardener, such as bis(vinylsulfonylmethyl)ether. These zones have been found to be useful in the manufacturing process in order to prevent blocking between one zone and another.

Another type of zone that is particularly useful in these elements is known as a radiation-blocking zone. Such zones are also known in the art and have been described, for example, in U.S. Pat. No. 4,042,335 and U.S. Pat. No. 4,166,093. A radiation-blocking zone is a zone that is permeable to a predetermined analyte (or a reaction product thereof) and that reflects, or, optionally, absorbs, detecting radiation. The radiation-blocking zone can be used to screen spectral interferences in addition to providing increased reflectivity. These zones provide increased dynamic range of the assay owing to lower background densities and also provide a means for screening chromogenic (spectral) interferences that absorb in the same wavelength region in which the assay is monitored. For example, the conventional dye-detection system for glucose, utilizing 4-aminoantipyrine and 1,7-dihydroxynaphthalene, absorbs at the same wavelength as hemoglobin, a serious chromogenic interferent. By using the radiation-blocking zone, only the dye located below the radiation-blocking zone, and not the hemoglobin, is detected.

The use of a radiation-blocking zone together with the barrier zone in the elements of the present invention permits a wide choice of wavelengths for the assay, ranging from 250 to 900 nm.

Still other zones that can be employed in the present elements include registration zones, detectable species migration-inhibiting zones, filtering zones, and the like, such as those that have been described in U.S. Pat. No. 3,992,158; U.S. Pat. No. 4,042,335; U.S. Pat. No. 4,066,403 (Reissue 30,267); and U.S. Pat. No. 4,166,093.

The above-described zones, when combined, can be self-supporting or can be carried on a support. Useful support materials include a variety of polymers, such as cellulose acetate; polyethylene terephthalate; polycarbonates; and polyvinyl compounds, such as polystyrene; glass or metal; and paper. A support of choice for any particular element will be compatible with the intended mode of result detection. For example, for fluorimetric detection wherein fluorimetric emission within the element is detected as the emission is transmitted from within the element through the support to an external detector, it is desirable to employ as a support material a material that exhibits a low degree of background fluorimetric emission. Thus, preferred supports include supports that are radiation-transmissive with respect to the particular radiation employed to provide detectable changes within the element.

Preferably, the various zones referred to above are present in the elements of the present invention as superposed contiguous layers.

Materials

In the examples below, whole blood samples were obtained from local medical facilities. Alkanol XC (sodium alkyl naphthalene sulfonate) and Zonyl FSN (a fluorochemical surfactant) were obtained from DuPont, Wilmington, DE. Polyvinyl pyrrolidone was obtained from GAF Corporation, Atlanta, GA. Triton X-100 was purchased from Rohm and Haas of Philadelphia, PA. Glucose oxidase was purchased from Sigma, St. Louis, MO, and peroxidase was purchased from Miles Laboratories, Elkhart, IN. All other compounds were obtained from Eastman Kodak Company, Rochester, NY, and, unless otherwise noted, were of reagent grade.

Methods

Whole blood samples were prepared for patient calibration tests according to the following procedures to obtain a broad dynamic range:

Low glucose level samples (below 80 mg/dL) were diluted or depleted according to the following methods:

(1) plasma was removed from centrifuged samples and replaced with HSA (human serum albumin) and saline to keep the electrolyte balance or (2) glycolysis was allowed to occur.

High glucose level samples (above 80 mg/dL) were prepared by the addition of glucose.

| General Element Formats: | |
| --- | --- |
| I Spreading Layer | II Spreading Layer |
| Binder Layer (optional) | Binder Layer (optional) |
| Gel Pad Layer (optional) | Radiation-Blocking Layer (optional) |
| Barrier Layer | Barrier Layer |
| Reagent Layer | Reagent Layer |
| Support (optional) | Support (optional) |

EXAMPLE 1

No Barrier Zone (Comparative Example)

Test Element I was prepared as follows: a polyethylene terephthalate support was overcoated with a reagent zone comprising [2(3,5-dimethoxy-4-hydroxyphenyl)-4,5-bis(4-dimethylaminophenyl)imidazole] (a leuco dye), dimedone, 2,4-di-n-pentylphenol, deionized gelatin, poly(methyl acrylate-co-2-acrylamido-2-methylpropane sulfonic acid-co-2-acetoacetoxyethyl methacrylate), weight ratio 88.8/4.7/6.5, Zonyl FSN, peroxidase (POD), glucose oxidase (GOD), dimethyl glutaric acid (DMG) (pH 6.0), and bis(vinyl sulfonylmethyl ether) (BVSME); and a spreading zone comprising poly(vinyl toluene-co-p-t-butylstyrene-co-methacrylic acid) beads, weight ratio 61/37/2, 20–40$\mu$ in diameter, poly(n-butyl acrylate-co-styrene-co-2-acrylamido-2-methylpropane sulfonic acid) weight ratio 76/19/5, and Zonyl FSN.

The element was spotted with 10 $\mu$L aliquots of three whole blood samples having glucose levels of 88, 199, and 392 mg/dL, respectively. The reaction was monitored at room temperature using a spectrophotometer by measuring reflectance densities at 800 nm over a 7 minute period. No meaningful distinctions among the glucose levels tested could be obtained with this element.

EXAMPLE 2

No Barrier Zone (Comparative Example)

Test Element II was prepared as follows: a polyethylene terephthalate support was overcoated with a reagent zone comprising [2(3,5-dimethoxy-4-hydroxyphenyl)-4,5-bis(4-dimethylaminophenyl)-imidazole], poly(methyl acrylate-co-2-acrylamido-2-methylpropane sulfonic acid-co-2-acetoacetoxyethyl methacrylate) weight ratio 88/5/7, deionized gelatin, 2,4-di-n-pentylphenol, dimedone, Zonyl FSN, 3,3-dimethylglutaric acid (pH 6.0), peroxidase, glucose oxidase, and BVSME. A second zone was coated over the reagent zone and comprised 1.1 gm/m$^2$ (100 mg/ft$^2$) of deionized gelatin, 0.048 gm/m$^2$ (4.5 mg/ft$^2$) of Zonyl FSN, and 0.019 gm/m$^2$ (1.75 mg/ft$^2$) of BVSME. A spreading zone was coated over the second zone and comprised poly(vinyl toluene-co-p-t-butylstyrene-co-methacrylic acid) beads, weight ratio 61/37/2, 20–40$\mu$ in diameter, poly(n-butylacrylate-co-styrene-co-2-acrylamido-2-methyl propane sulfonic acid) sodium salt, weight ratio 70/20/10, Kelzan (a xanthan gum thickener commercially available from Kelco Co.), and Zonyl FSN.

The element was spotted with whole blood samples having glucose levels of 66, 131, 229, 309, 408, and 588 mg/dL. The results were poor with crossover being exhibited for the 131 and 229 mg/dL samples and for the 588 mg/dL sample with the 309 and 408 mg/dL samples. By "crossover" we mean that graphs of reflection density vs. time for two or more different concentrations intersect, or "crossover" one another. Readings were made at 700 nm and over a 5 minute period.

This shows that a "barrier" layer prepared from gelatin, as described, for example, in U.K. Published Application; 2,069,131 A, is not useful.

EXAMPLE 3

Barrier Zone

Test Element III was prepared having the same reagent and spreading zones as those of Test Element II in Example 2.

A barrier zone of the present invention was substituted for the "second zone" of Example 2, however, by replacing the 1.1 gm/m$^2$ (100 mg/ft$^2$) of deionized gelatin with 0.90 gm/m$^2$ (84 mg/ft$^2$) of poly(n-butyl methacrylate-co-2-methacryloyloxyethyl-1-sulfonic acid-co-2-acetoacetoxyethyl metharcylate-co-2-hydroxyethyl methacrylate) sodium salt, weight ratio 60/5/10/25, and 0.17 gm/m$^2$ (16 mg/ft$^2$) of deionized gelatin. Zonyl FSN and BVSME were also present in this zone in the same concentration as in Element II.

The element was spotted with whole blood samples having glucose levels of 57, 107, 227, 372, 478, and 623 mg/dL. Good distinction between levels was obtained and the levels were distinguished in the proper order, i.e., low to high glucose, indicating that the barrier zone had successfully screened the chemical interferents. Readings were made at 700 nm and over a 5 minute period.

EXAMPLE 4

Barrier Zone

Test Element IV was prepared according to general format I, shown above, and comprised the following zones, each coated over the preceding zone. A polyethylene terephthalate support was coated with a reagent zone comprising: [2(3,5-dimethoxy-4-hydroxyphenyl)-4,5-bis(4-dimethylaminophenyl)imidazole], dimedone, 2,4-di-n-pentylphenol, deionized gelatin, Zonyl FSN, BVSME, peroxidase, glucose oxidase, dimethyl glutaric acid (pH 6.0), and poly(methyl acrylate-co-2-acrylamido-2-methylpropane sulfonic acid-co-2-acetoacetoxyethyl methacrylate, weight ratio 88.8/4.7/6.5; a barrier zone comprising poly(n-butyl methacrylate-co-2-methacryloxyethyl-1-sulfonic acid-co-2-acetoacetoxyethyl methacrylate-co-2-hydroxyethyl methacrylate) sodium salt weight ratio 60/5/10/25, (0.5 g/m$^2$), deionized gelatin (0.04 g/m$^2$), and Zonyl FSN (0.05 g/m$^2$); a gel pad zone comprising deionized gelatin, Zonyl FSN and BVSME; a binder zone comprising poly(vinyl pyrrolidone); and a spreading zone comprising poly(vinyl toluene-co-p-t-butyl styrene-co-methacrylic acid) beads, weight ratio 61/37/2, 20–40μ in diameter, poly(acrylamide), and Triton X-100.

The element was spotted with 10 μL aliquots of four whole blood samples having glucose levels of 66, 105, 214, and 408 mg/dL, respectively. The reaction was monitored at room temperature using a spectrophotometer by measuring reflectance densities at 700 nm over a 7 minute period. Good distinction between levels was obtained and the levels were distinguished in the proper order, i.e., low to high glucose.

EXAMPLE 5

Barrier and Radiation-Blocking Zones

Test Element V was prepared according to general format II, described above, and was prepared in the same manner as Test Element IV, except that a radiation-blocking zone was coated over the barrier zone and the gel pad zone was excluded. The radiation-blocking zone comprised titanium dioxide, gelatin, Zonyl FSN, and BVSME.

The test procedure was identical to that in Example 4. Compared with the results of Example 4, background density was greatly diminished by the radiation-blocking zone, and the discrimination between glucose levels improved, especially at the higher levels where more density is observed.

EXAMPLE 6

Polymer Variations in the Barrier Layer

Test Elements VI-X, with variations in the polymer used in the barrier zone, were evaluated for performance in the discrimination of glucose levels in whole blood. All elements were spotted with whole blood samples (10 μL aliquots). The reactions were monitored at 720 nm over a 3 minute period at 25° C., using a spectrophotometer.

A. Poly(n-butyl methacrylate-co-2-methacryloyloxy-ethyl-1-sulfonic acid-co-2-acetoacetoxyethyl methacrylate-co-2-hydroxyethyl methacrylate) sodium salt, weight ratio 60/5/10/25 (12:1, polymer:gelatin)

Test Element VI was prepared according to format I above in the following manner: a polyethylene terephthalate support was overcoated with a reagent zone; a barrier zone as described in Example 4 comprising the above polymer, except that the barrier zone also contained BVSME (0.01 g/m$^2$); a gel pad zone comprising deionized gelatin, Zonyl FSN, and BVSME; and a spreading zone comprising the polymer beads of Example 4, Zonyl FSN, poly(n-butyl acrylate-co-styrene-co-2-acrylamido-2-methyl propane sulfonic acid), weight ratio 76/19/5; and Kelzan.

Excellent calibration of the element was demonstrated, with glucose levels ranging from ~40–~410 mg/dL, indicating this polymer along with gelatin is especially suitable in the barrier zone of the present invention.

B. Poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio 70/2.5/10/17.5 (12:1, polymer:gelatin)

Test Element VII was prepared according to format I, described earlier, as follows: a reagent zone, comprising deionized gelatin, leuco dye, 2,4-di-n-pentylphenol, dimedone, Zonyl FSN, BVSME, dimethyl glutaric acid (pH 6.0), peroxidase, and glucose oxidase was coated over a polyethylene terephthalate film support. A barrier zone, comprising poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio 70/2.5/10/17.5 (0.5 g/m$^2$), deionized gelatin (0.04 g/m$^2$), Zonyl FSN (0.05 g/m$^2$), and BVSME (0.01 g/m$^2$) was coated over the reagent zone. Finally, a spreading zone comprising beads of poly(vinyl toluene-co-p-t-butylstyrene-co-methacrylic acid) weight ratio 61/37/2, 20–40μ in diameter, Zonyl FSN, Kelzan, and poly(n-butyl acrylate-co-styrene-co-2-acrylamido-2-methyl propane sulfonic acid), weight ratio 70/20/10, was coated over the barrier zone.

Good discrimination between glucose levels ranging from ~30–~400 mg/dL in whole blood samples was demonstrated indicating the usefulness of this polymer along with gelatin in the barrier zone of the present invention.

C. Poly(2-ethylhexyl methacrylate-co-2-methacryloyloxyethyl-1-sulfonic acid-co-2-acetoacetoxyethyl methacrylate-co-2-hydroxyethyl methacrylate) sodium salt, weight ratio 50/2.5/10/37.5 (12:1, polymer:gelatin)

Test Element VIII was prepared according to format I, described above, differing from Test Element VI as follows: the barrier zone comprised poly(2-ethylhexyl methacrylate-co-2-methacryloyloxyethyl-1-sulfonic acid-co-2-acetoacetoxyethyl methacrylate-co-2-hydroxyethyl methacrylate) sodium salt, weight ratio 50/2.5/10/37.5, (0.5 g/m$^2$), deionized gelatin (0.04 g/m$^2$), Triton X-100 (0.05 g/m$^2$), and BVSME (0.01 g/m$^2$); and the gel pad zone comprised deionized gelatin, BVSME, and Triton X-100.

Samples tested ranged from ~40–~420 mg/dL glucose. The calibration results demonstrated that this polymer along with gelatin is also suitable for use in the barrier zone of the present invention.

D. Poly(n-butyl methacrylate-co-2-aminoethyl methacrylate hydrochloride-co-2-hydroxyethyl methacrylate), weight ratio 50/15/35 (1:1, gel:polymer)

Test Element IX was prepared according to format I, described above, as follows: a reagent zone, as described above, was coated over a polyethylene terephthalate support. A barrier zone comprising poly(n-butyl methacrylate-co-2-aminoethyl methacrylate hydrochloride-co-2-hydroxyethyl methacrylate), weight ratio 50/15/35, (0.5 g/m$^2$), deionized gelatin (0.5 g/m$^2$), and Zonyl FSN (0.05 g/m$^2$) surfactant was coated over the reagent zone. A spreading zone, as described above, was coated over the barrier zone.

The test element was evaluated using whole blood samples with glucose levels ranging from ~30–~285 mg/dL. Reflectance densities were monitored. The calibration results demonstrated this polymer along with gelatin (in a 1:1 ratio) to be useful in the barrier zone of the present invention.

E. Poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio 70/2.5/10/17.5 (100% polymer and no gelatin)

Test Element X was prepared to evaluate the barrier zone performance without gelatin in that zone. The element was prepared according to format I as follows: the reagent zone had the same composition as that zone in test Element VII, except that the BVSME concentration was approximately doubled; the barrier zone comprised poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio 70/2.5/10/17.5, (0.5 g/m$^2$), Zonyl FSN (0.05 g/m$^2$), and BVSME (0.01 g/m$^2$); and the spreading zone comprised beads of poly(vinyl toluene-co-p-t-butyl styrene-co-methacrylic acid), weight ratio 61/37/2, 20-40$\mu$ in diameter, Zonyl FSN, and poly(n-butyl acrylate-co-styrene-co-2-acrylamido-2-methyl propane sulfonic acid), weight ratio 70/20/10.

The test element was spotted with 10 $\mu$L aliquots of three whole blood samples having glucose levels of 86, 191, and 403 mg/dL, respectively. The reaction was monitored at room temperature using a spectrophotometer by measuring reflectance densities at 800 nm over a 7 minute period. After about 4-5 minutes, the results obtained showed improvement over elements that were similar but had no barrier layer in that distinctions between the glucose levels could be observed. The results, however, were inferior to those obtained where gelatin was present in the barrier zone.

EXAMPLE 7

Patient Calibration of the Dry Element Using the Poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio 60/5/10/25 Barrier Zone The dry element for whole blood glucose, Test Element VI having a poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio of 60/5/10/25, was calibrated using patient samples ranging in glucose levels from ~54-~354 mg/dL. Test Element VI was prepared as described in Example 6. The assays also were carried out as described in Example 6, except that the patient samples were used as their own references.

The calibration results representing patient data obtained over a three-day period demonstrated that the improved elements of the present invention are effective in determining whole blood glucose.

EXAMPLE 8

Barrier Layer Effects on Determination of Glucose on Whole Blood vs Slightly Hemolyzed Plasma vs Grossly Hemolyzed Plasma

A. No Barrier Zone

Test elements were prepared as described in Example 1 (containing no barrier zone). The elements were spotted with 10 $\mu$L samples having glucose levels ranging from ~80-~430 mg/dL in various matrices as shown in Table I.

TABLE I

| Glucose Level mg/dL | Matrix | | |
|---|---|---|---|
| | Whole Blood | Slightly (1) Hemolyzed Plasma | Grossly (2) Hemolyzed Plasma |
| 80 | | X | X |
| 88 | X | | |
| 199 | X | | |
| 232 | | X | X |
| 392 | X | | |
| 431 | | X | X |

(1) "Slightly Hemolyzed Plasma" is the equivalent of about 50 mgs/deciliter of hemoglobin.
(2) "Grossly Hemolyzed Plasma" is the equivalent of about 7 gms/deciliter of hemoglobin.

No meaningful distinction between the glucose levels tested was obtained especially at early read times, regardless of matrix, i.e., whole blood or lysed red cells in plasma.

B. With Barrier Zone

Test elements were prepared according to the following: A polyethylene terephthalate film support was coated with a reagent zone comprising gelatin, BVSME, leuco dye (as in Example 1), Zonyl FSN, POD, GOD, dimedone, di-n-pentylphenol, and DMG at pH 6.0; a barrier zone comprising poly(n-butyl methacrylate-co-2-methacryloyloxyethyl-1-sulfonic acid-co-2-acetoacetoxyethyl methacrylate-co-2-hydroxyethyl methacrylate) sodium salt, weight ratio 70/2.5/10/17.5 (0.5 g/m$^2$) and gelatin (0.04 g/m$^2$); and a spreading zone comprising the polymer beads of Example 1, 20-40$\mu$ in diameter, 2% by weight poly(n-butyl acrylate-co-styrene-co-2-acrylamido-2-methyl propane sulfonic acid), weight ratio 70/20/10, and Zonyl FSN.

Good distinction between glucose levels tested was obtained regardless of matrix.

EXAMPLE 9

Poly(n-butyl methacrylate-co-2-aminoethylmethacrylate hydrochloride-co-2-hydroxyethylmethacrylate) (wt. ratio 50/15/35): gelatin, 2:3 weight ratio Test elements for the determination of whole blood glucose were prepared as described in Example 6D except that the barrier layer comprised poly(n-butyl methacrylate-co-2-aminoethyl methacrylate hydrochloride-co-2-hydroxyethylmethacrylate) (50/15/35) and gelatin in the ratio of 2:3 (instead of 1:1). Surfactant, Zonyl FSN (0.08 g/m$^2$), and hardener, BVSME (0.06 g/m$^2$), were also included in that layer. The results indicated good discrimination between glucose values of from 76 to 554 mg/dL.

EXAMPLE 10

Poly(n-butyl methacrylate-co-2-methacryloyloxyethyl-1-sulfonic acid-co-2-acetoacetoxyethyl methacrylate-co-2-hydroxyethyl methacrylate) sodium salt (wt. ratio 60/5/10/25): gelatin, 7:1 weight ratio.

Test elements were prepared as described in Example 6B except that the polymer:gelatin weight ratio was 7:1 (instead of 12:1) and the weight ratio of the monomers polymerized to form the polymer of the barrier zone was 60/5/10/25 (instead of 70/2.5/10/17.5).

The results showed good discrimination of glucose levels from 58 to 600 mg/dL using this higher proportion of gelatin.

EXAMPLE 11

Comparative Example Cellulose Acetate Butyrate (CAB) as Barrier Zone Composition in Glucose Element (as disclosed in U.S. Pat. No. 4,258,001)

A test element was prepared by overcoating a polyethylene terephthalate support with a reagent zone comprising gelatin, poly(methacrylate-co-2-acrylamido-2-methylpropane sulfonic acid-co-2-acetoacetoxyethyl methacrylate) weight ratio 88.8/4.7/6.5, Alkanol XC, DMG, dimedone, 4-isopropoxy-1-naphthol, poly(n-butylmethacrylate-co-styrene-co-2-acrylamido-2-m ethyl propane sulfonic acid) weight ratio 50/40/10, GOD, POD, and BVSME. A second zone, to be tested for barrier properties, comprising cellulose acetate butyrate (0.54 gm/m²) was coated over the reagent zone. Finally, a spreading zone was coated over the second zone comprising poly(vinyl toluene-co-p-t-butylstyrene-co-methacrylic acid) beads, weight ratio 61/37/2, 40-45μ in diameter, poly(n-butyl acrylate-co-styrene-co-2-acrylamido-2-methylpropane sulfonic acid) weight ratio 76/19/5, and Zonyl FSN.

The elements were tested as above using 77, 177, and 370 mg/dL glucose, respectively, and reflectance densities were monitored at 720 nm for >5 min. The results indicated that no discrimination between glucose levels was obtained using CAB as the barrier zone.

EXAMPLE 12

Comparative Example

| Comparative Example Ethyl Cellulose as Barrier Zone (As in U.K. Patent 922,665) Composition in Glucose Element Element format: | | | | |
|---|---|---|---|---|
| Spreading Zone | Beads of Example 1 (20-40μ) Poly(n-isopropyl acrylamide) Triton X-100 Poly(vinyl pyrrolidone) | | | |
| Barrier Zone | Ethyl Cellulose | | | |
| | 0.54 g/m² | 1.1 g/m² | 2.2 g/m² | 4.3 g/m² |
| | Elememt D | Element E | Element F | Element G |
| Reagent Zone | Leuco dye Dimedone Di-n-pentylphenol Gelatin Zonyl FSN POD GOD DMG BVSME Poly(methylacrylate-co-2-acrylamido-2-methyl-propane sulfonic acid-co-2-acetoacetoxyethyl methacrylate) weight ratio 88.8/4.7/6.5 Poly(ethylene terephthalate) support | | | |

Elements D through G were tested and evaluated as above using glucose concentrations of 50, 110, 210, 315, and 400 mg/dL, respectively. The elements were monitored at 700 nm for 5 min. Elements D, E, and F demonstrated very poor discrimination with crossover between some of the analyte concentrations. Element G, which comprises the highest level of barrier material used (4.3 g/m²), showed a tendency towards discrimination between glucose levels, but had lost considerable density and therefore sensitivity, making this amount of material unsuitable.

EXAMPLE 13

Comparative Example

The following polymers were also prepared and tested in the manner of the previous examples and found to be unsuitable as barrier layers for use in the present invention.

A. Poly(n-butyl acrylate-co-2-acrylamido-2-methylpropane sulfonic acid, sodium salt-co-2-acetoacetoxyethyl methacrylate) (Wt. Ratio 90:6:4)

B. Poly(methylacrylate-co-2-acrylamide-2-methylpropane sulfonic acid, sodium salt-co-2-acetoacetoxyethyl methacrylate) (Wt. Ratio 90:4:6)

C. Poly(n-isopropyl acrylamide)

D. Poly(n-isopropyl acrylamide-co-acrylamide) (Wt. Ratio 90:10)

E. Poly(n-isopropyl acrylamide-co-acrylamide-co-2-acetoacetoxyethyl methacrylate) (Wt. Ratios 80:10:10, 75:15:10, 70:20:10)

F. Poly(acrylamide-co-x-(2-chloroethyl sulfonyl methyl)styrene x-vinyl toluene, 2-chloroethyl sulfone (Wt. Ratio 95:5)

G. Poly[ethylene-co-4,4'-isopropylidenebis(-phenyleneoxyethylene) (Mole % 50:50) 5-(4-sodiosulfophenoxy)-1,3-benzenedicarboxylate-co-terephthalate (Mole % 50:50)]

H. Poly[ethylene-co-4,4'-isopropylidenebis(-phenyleneoxyethylene) (Mole % 50:50) isophthalate-co-(4-sodiosulfophenoxy)-1,3-benzenedicarboxylate (Mole % 50:50)]

The invention has been described in detail with particular reference to certain preferred embodiments thereof, but it will be understood that variations and modifications can be effected within the spirit and scope of the invention.

What is claimed is:

1. A multizone element, for quantitative analyte determination in whole blood, containing a porous spreading zone separated from a reagent zone by a barrier zone, said barrier zone comprising a non-porous film comprising a polymer of from 30 to 95 percent by weight polymerized monomer having the structure

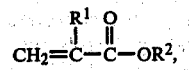

from 0.25 to 30 percent by weight polymerized monomer having the structure

from 0.1 to 50 percent by weight polymerized monomer having the structure

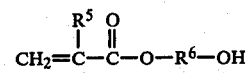

wherein:
$R^1$, $R^3$, and $R^5$ are independently selected from the group consisting of hydrogen and methyl,
$R^2$ is alkyl of from 1 to 16 carbon atoms, $R^4$ and $R^6$ are independently selected from the group consisting of alkylene groups having from 1 to 6 carbon atoms,

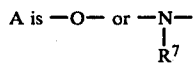

wherein $R^7$ is hydrogen, alkyl of 1 to 10 carbon atoms, or cycloalkyl of 5 to 10 carbon atoms, and M is $NR^8R^9H^+X$ or $SO_3^-X$ wherein $R^8$ and $R^9$ are independently selected from the group consisting of hydrogen and alkyl of 1 to 4 carbon atoms and X is a counterion.

2. The element of claim 1 wherein the barrier zone further comprises up to 70% by weight of gelatin, based upon the combined weight of the polymer and the gelatin.

3. The element of claim 1 wherein the polymer further comprises up to about 20 percent by weight of a polymerized monomer containing an active methylene group in a side chain.

4. The element of claim 1 wherein the reagent zone includes a reagent for glucose.

5. The element of claims 1, 2, 3, or 4 wherein A is —O— and $R^8$ and $R^9$ are both hydrogen.

6. The element of claims 1, 2, 3, or 4 wherein the polymerized monomer of the structure

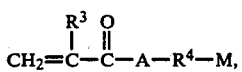

is selected from the group consisting of 2-methacryloyloxyethyl-1-sulfonic acid, sodium salt; sodium 3-acryloyloxypropane sulfonate; sodium 2-acrylamido-2-methylpropane sulfonate; and 2-aminoethyl methacrylate hydrochloride.

7. The element of claims 1, 2, 3, or 4 wherein the polymer is selected from the group consisting of poly(n-butyl methacrylate-co-2-methacryloyloxyethyl-1-sulfonic acid-co-2-acetoacetoxyethyl methacrylate-co-2-hydroxyethyl methacrylate); poly(2-ethylhexyl methacrylate-co-methacryloyloxy-ethyl-1-sulfonic acid-co-2-acetoacetoxyethyl methacrylate-co-2-hydroxyethyl methacrylate); and poly(n-butyl methacrylate-co-2-aminoethyl methacrylate hydrochloride-co-2-hydroxyethyl methacrylate).

8. A process, for quantitative analyte determination in whole blood, comprising bringing a sample of the blood into contact with a multizone element containing a porous spreading zone separated from a reagent zone by a barrier zone, said barrier zone comprising a non-porous film comprising a polymer of from 30 to 95 percent by weight polymerized monomer having the structure

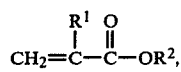

from 0.25 to 30 percent by weight polymerized monomer having the structure

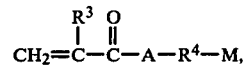

from 0.1 to 50 percent by weight polymerized monomer having the structure

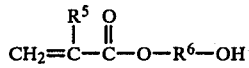

wherein:
$R^1$, $R^3$, and $R^5$ are independently selected from the group consisting of hydrogen and methyl,
$R^2$ is alkyl of from 1 to 16 carbon atoms,
$R^4$ and $R^6$ are independently selected from the group consisting of alkylene groups having from 1 to 6 carbon atoms,

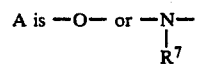

wherein $R^7$ is hydrogen, alkyl of 1 to 10 carbon atoms, or cycloalkyl of 5 to 10 carbon atoms, and M is $NR^8R^9H^+X$ or $SO_3^-X$ wherein $R^8$ and $R^9$ are independently selected from the group consisting of hydrogen and alkyl of 1 to 4 carbon atoms and X is a counterion.

9. The process of claim 8 wherein the barrier zone further comprises up to 70% by weight of gelatin, based upon the combined weight of the polymer and the gelatin.

10. The process of claim 8 wherein the polymer further comprises up to about 20 percent by weight of a polymerized monomer containing an active methylene group in its side chain.

11. The process of claim 8 wherein the analyte being determined is glucose.

12. The process of claims 8, 9, 10, or 11 wherein A is —O— and $R^8$ and $R^9$ are both hydrogen.

13. The process of claims 8, 9, 10, or 11 wherein the polymerized monomer of the structure

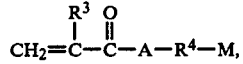

is selected from the group consisting of 2-methacryloyloxyethyl-1-sulfonic acid, sodium salt; sodium 3-acryloyloxypropane sulfonate; sodium 2-acrylamido-2-methylpropane sulfonate; and 2-aminoethyl methacrylate hydrochloride.

14. The process of claims 8, 9, 10, or 11 wherein the polymer is selected from the group consisting of poly(n-butyl methacrylate-co-2-methacryloyloxyethyl-1-sulfonic acid-co-2-acetoacetoxy-ethyl methacrylate-co-2-hydroxyethyl methacrylate); poly(2-ethylhexyl methacrylate-co-methacryloyloxy-ethyl-1-sulfonic acid-co-2-acetoacetoxyethyl methacrylate-co-2-hydroxyethyl methacrylate); and poly(n-butyl methacrylate-co-2-aminoethyl methacrylate hydrochloride-co-2-hydroxyethyl methacrylate).

* * * * *